(12) United States Patent
Fukutani (10) Patent No.: US 9,560,973 B2
(45) Date of Patent: Feb. 7, 2017

(54) SUBJECT INFORMATION ACQUIRING DEVICE AND SUBJECT INFORMATION ACQUIRING METHOD

(75) Inventor: Kazuhiko Fukutani, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 678 days.

(21) Appl. No.: 13/990,528

(22) PCT Filed: Dec. 13, 2011

(86) PCT No.: PCT/JP2011/079280
§ 371 (c)(1),
(2), (4) Date: May 30, 2013

(87) PCT Pub. No.: WO2012/090742
PCT Pub. Date: Jul. 5, 2012

(65) Prior Publication Data
US 2013/0245420 A1    Sep. 19, 2013

(30) Foreign Application Priority Data

Dec. 27, 2010 (JP) .................................. 2010-290254

(51) Int. Cl.
*A61B 5/00* (2006.01)
(52) U.S. Cl.
CPC .............. *A61B 5/0095* (2013.01); *A61B 5/72* (2013.01)
(58) Field of Classification Search
None
See application file for complete search history.

(56) References Cited

U.S. PATENT DOCUMENTS 6,043,884 A * 3/2000 Curbelo ............... G01J 3/447
356/451
7,864,307 B2   1/2011 Fukutani et al.
(Continued)

FOREIGN PATENT DOCUMENTS

WO    WO 00/45707    8/2000

OTHER PUBLICATIONS

T. Lu et al., "Deconvolution Algorithm with LTI Wiener Filter in Photoacoustic Tomography", *Photonics and Optoelectronics*, vol. 1, pp. 1-4 XP031524325 (Aug. 14, 2009).
(Continued)

*Primary Examiner* — Long V Le
*Assistant Examiner* — Bradley Impink
(74) *Attorney, Agent, or Firm* — Fitzpatrick, Cella, Harper & Scinto (57) ABSTRACT

A subject information acquiring device which has: an light absorbing member provided outside a subject; a light source radiating pulsed light on the subject and the light absorbing member; a detector detecting an acoustic wave produced from the subject and the light absorbing member by means of the pulsed light; and a signal processing unit acquiring subject information using a detection signal, and the signal processing unit calculates a second detection signal by specifying a signal resulting from an acoustic wave produced from the light absorbing member in a first detection signal, acquiring impulse response data using the specified signal, and deconvoluting the first detection signal using the impulse response data, and acquires the subject information using the second detection signal, can reduce image deterioration due to probe characteristics even when an impulse response of a probe is not measured in advance in a photoacoustic tomography.

19 Claims, 4 Drawing Sheets

(56) References Cited

U.S. PATENT DOCUMENTS

| | | |
|---|---|---|
| 7,916,283 B2 | 3/2011 | Fukutani et al. |
| 2004/0039379 A1* | 2/2004 | Viator .................. A61B 18/203 606/9 |
| 2013/0006088 A1* | 1/2013 | Miyasato ............. A61B 5/0073 600/407 |

OTHER PUBLICATIONS

R. Kruger et al., "Thermoacoustic Computed Tomography—Technical Considerations", The American Association of Physicists in Medicine, *Medical Physics,* vol. 26(9), pp. 1832-1837 XP012010891 (Sep. 1999).

M. Xu et al., "Photoacoustic Imaging in Biomedicine", American Institute of Physics, *Review of Scientific Instruments,* vol. 77, pp. 041101-1 to 041101-22 (Apr. 17, 2006).

* cited by examiner

SUBJECT INFORMATION ACQUIRING DEVICE AND SUBJECT INFORMATION ACQUIRING METHOD

TECHNICAL FIELD

The present invention relates to a subject information acquiring device and a subject information acquiring method. More particularly, the present invention relates to a subject information acquiring device and a subject information acquiring method which detect an acoustic wave produced from an interior of a subject by radiating light on the subject and acquire information about the interior of the subject as image data.

BACKGROUND ART

A study on an optical imaging device which radiates light on a biological body from a light source such as a laser and converts information about an interior of the biological body obtained based on incident light into an image is actively advanced in a medical field. As one of optical imaging techniques, there is a photoacoustic tomography (PAT). The photoacoustic tomography refers to a technique of radiating pulsed light, produced from a light source, on a biological body, and detecting and analyzing an acoustic wave (typically, ultrasound) produced by biological tissues which absorbed energy of pulsed light having propagated and diffused in the biological body to visualize intra-subject information. More specifically, by utilizing the difference in the absorptance of optical energy between a subject site such as a tumor and tissues other than the subject site, an acoustic detector (referred to as "probe" or "transducer") receives an elastic wave which is produced when the subject site absorbs optical energy radiated on the subject site and instantaneously expands. By mathematically analyzing this detected signal, an initial acoustic pressure distribution or an optical characteristic distribution in the biological body, particularly, an absorption coefficient distribution, can be obtained. These pieces of information can be also utilized to quantitatively measure specific substances in the subject such as a hemoglobin concentration included in blood or oxygen saturation in blood by using lights of various wavelengths. In recent years, using this photoacoustic tomography, a pre-clinical study of imaging blood vessel images of small animals or clinical study of applying this principle to diagnosis of, for example, breast cancer, are actively advanced (NPL 1).

In an acoustic wave probe which is usually used in a photoacoustic tomography device, a frequency of an acoustic wave to be detected is limited (band limitation). Hence, there is a problem that an image to be obtained may deteriorate when a normal image reconstruction method which assumes the ideal acoustic wave probe characteristics is used. In response to this problem, a method is proposed for decreasing the influence of a probe on image deterioration, by measuring in advance an impulse response of an acoustic wave probe (response characteristic data unique to an element) and correcting (for example, deconvoluting) the detection signal according to this impulse response (NPL 2).

CITATION LIST

Non Patent Literature

NPL 1: "Photoacoustic imaging in biomedicine", M. Xu, L. V. Wang, *REVIEW OF SCIENTIFIC INSTRUMENTS*, 77, 041101, 2006.

NPL 2: "Thermoacoustic Computed Tomography-Technical Consideration", R. A. Kruger, D. R. Reinecke, G. A. Kruger, *Medical Physics*, Vol. 26, No. 9, 1832-1837, 1999.

SUMMARY OF INVENTION

Technical Problem

However, in a conventional method, since an impulse response of the probe found in advance by measurement is continuingly utilized at all times, the method cannot support a characteristics change due to aging of the probe. In addition, the characteristic change described herein refers to a change of frequency characteristics or a sensitivity. In addition, it needs that, whenever the probe is changed, an impulse response for the frequency that the new probe can detect or for the detector size of the probe be laboriously obtained again.

The present invention is made based on this recognition of the problem. It is therefore an object of the present invention to reduce image deterioration due to varied probe characteristics, by correcting a detection signal using data equivalent to an impulse response to a probe obtained upon measurement, even when an impulse response of the probe is not measured in advance or probe characteristics deteriorate due to aging.

Solution to Problem

In light of the above problem, the subject information acquiring device according to the present invention has: an optical absorber which is provided outside a subject; a light source which radiates pulsed light on the subject and the optical absorber; a detector which detects an acoustic wave produced from the subject and the optical absorber by means of the pulsed light; and a signal processing unit which acquires subject information using a detection signal acquired from the detector, and the signal processing unit calculates a second detection signal by specifying a signal resulting from an acoustic wave produced from the optical absorber in a first detection signal acquired by the detector, acquiring impulse response data using the specified signal and deconvoluting the first detection signal using the impulse response data, and acquires the subject information using the second detection signal.

Advantageous Effects of Invention

According to the present invention, it is possible to reduce image deterioration due to varied probe characteristics, by correcting a detection signal using data equivalent to an impulse response to a probe obtained upon measurement, even when an impulse response of the problem is not measured in advance or probe characteristics deteriorate due to aging.

Further features of the present invention will become apparent from the following description of exemplary embodiments with reference to the attached drawings.

DESCRIPTION OF EMBODIMENTS

Hereinafter, the present invention will be described in more details with reference to the accompanying drawings. The same components will be basically assigned the same reference numerals to avoid duplicated explanations. Further, the present invention is by no means limited only to a single device, and the present invention also incorporates, for example, a method of acquiring subject information described in the following embodiment, and a program which causes a computer to execute this method.

(Subject Information Acquiring Device)

A configuration of a subject information acquiring device according to the present embodiment will be described with reference to FIG. 1. The subject information acquiring device according to the present embodiment acquires subject information related to an optical characteristic value inside a subject as image data. With the present invention, an acoustic wave typically is an ultrasound, which includes elastic waves referred to as a sound wave, ultrasound, acoustic wave, photoacoustic wave and optical ultrasound. A subject information acquiring device according to the present invention includes a device which utilizes a photoacoustic effect of radiating light (electromagnetic wave) on the subject, receiving an acoustic wave (typically, ultrasound) produced in the subject and acquiring the subject information as image data. The subject information to be acquired includes an acoustic wave source distribution produced by radiation of light, initial acoustic pressure distribution in the subject, optical energy absorption density distribution derived from the initial acoustic pressure distribution, absorption coefficient distribution and concentration information distribution of substances constituting tissues. The concentration information distribution of substances is, for example, an oxygen saturation distribution, or oxygenated and deoxygenated hemoglobin concentration distributions.

The subject information acquiring device according to the present embodiment has a light source 11, a light absorbing member 18, an acoustic wave probe 17 which is a detector for acoustic waves and a signal processing unit 20 as a basic hardware configuration. Pulsed light 12 emitted from the light source 11 is guided while being processed into a desired light distribution shape by an optical system 13 such as a lens, mirror, optical fibers and diffuser plate, and is radiated on a subject 15 such as a biological body. When an optical absorber (which eventually becomes an acoustic source) 14 such as blood vessels or light absorbing member 18 absorbs part of energy of light which has propagated inside the subject 15, thermal expansion of the optical absorber 14 or light absorbing member 18 produces an acoustic wave (typically, ultrasound) 16. This is also referred to as "photoacoustic wave". The acoustic wave 16 is detected by the acoustic wave probe 17, amplified or digitally converted in a signal converter 19 and then converted into image data of subject information in the signal processing unit 20.

(Light Source 11)

When the subject is a biological body, the light source 11 radiates with light having a specific wavelength to be absorbed by specific components which are detection targets among components constituting the biological body. The light source can be provided integrally with the subject information acquiring device according to the present embodiment, or it can be separated from the device and provided as a separate body. The light source is preferably a pulsed light source which can produce pulsed light at the order of several nanoseconds to several hundreds of nanoseconds. More specifically, the pulse width having about 10 nanoseconds is used to efficiently produce a photoacoustic wave. Since a great output can be obtained, a laser is preferably adopted for the light source. It is however also possible to use, for example, a light emitting diode instead of the laser. The laser includes various lasers such as a solid-state laser, gas laser, pigment laser or semiconductor laser. A radiation timing, waveform and intensity are controlled by a light source control unit (not illustrated).

With the present invention, when a subject is a biological body, the wavelength of the light source to be used is preferably a wavelength which allows light to propagate to the interior of the subject. More specifically, the wavelength is 500 nm or more and 1300 nm or less.

(Optical System 13)

Although the light 12 radiated from the light source 11 is guided to the subject while being processed into a desired light distribution shape by, typically, an optical component such as a lens or mirror, it is also possible to allow light to propagate using an optical waveguide such as optical fibers. The optical system 13 is formed with, for example, a mirror which reflects light, a lens which condenses and enlarges light and changes the shape of light, a diffuser plate which diffuses light, and optical fibers. Any components may be used for these optical components as long as the light 12 emitted from the light source has a desired shape when it is radiated on the subject 15. It is more preferable to expand light to an area of a certain degree, rather than condensing by means of the lens, from the view points of securing safety for the biological body and expanding a diagnosis area.

To efficiently propagate optical energy to the subject, the optical system 13 can preferably radiate light on a subject surface 22 directly below the detection face of the acoustic wave probe 17. Further, although not illustrated, to propagate more optical energy to the subject, the optical system 13 can also preferably radiate light on the subject from a direction of the subject surface on the opposite side of the acoustic wave probe 17. Furthermore, the area of the subject on which light is radiated is preferably movable. In other words, the subject information acquiring device according to the present invention is preferably configured to radiate light produced from a light source on a plurality of areas on the subject by moving the optical system 13. When the optical system 13 is movable, it is possible to radiate light on a wider range. Further, the area of the subject on which light is radiated (light radiated on the subject) is preferably moved in synchronization with the acoustic wave probe 17. By this means, it is possible to convert an area of a wider range into an image. In addition, a method of moving the area of the subject on which light is radiated includes, for example, a method using, for example, a movable mirror and a method of mechanically moving the light source itself.

(Subject 15 and Optical Absorber 14)

Although these components do not form part of the subject information acquiring device, they will be described below. The subject information acquiring device according to the present invention is mainly directed to diagnosing malignant tumors and blood vessel disease of humans and animals, and a follow-up of a chemotherapy. Hence, the subject 15 is assumed to be a biological body and, more specifically, target sites such as breasts, fingers, hands and feet of the human body or animals. In case of small animals such as mice and rats, targets include not only specific sites but also whole small animals. The optical absorber 14 inside the subject refers to an optical absorber absolutely indicating a high absorption coefficient in the subject, and corresponds to, for example, oxygenated or deoxygenated hemoglobin, a blood vessel including these or a malignant tumor including many new blood vessels when the human body is a measurement target although it depends on the wavelength of light to be used. The optical absorber of the subject surface 22 further includes, for example, melanin near a skin surface.

(Acoustic Wave Probe 17)

The acoustic wave probe 17 which is a detector for detecting an acoustic wave produced from the subject surface or inside the subject by means of pulsed light, detects an acoustic wave, and converts the acoustic wave into an electrical signal which is an analog signal. Hereinafter, the acoustic wave probe 17 will be also referred to simply as "probe" or "transducer". Any acoustic wave detector such as transducers using piezoelectric phenomenon, resonance of light and a change of capacity may be used as long as they can detect acoustic wave signals. In the probe 17 according to the present embodiment, preferably, a plurality of receiving elements are provided in a one-dimensional or two-dimensional arrangement. By using such multi-dimensional alignment elements, it is possible to detect acoustic waves at a plurality of sites simultaneously, and reduce the measurement time. Consequently, it is possible to reduce an influence such as vibration of the subject.

Figure 1:
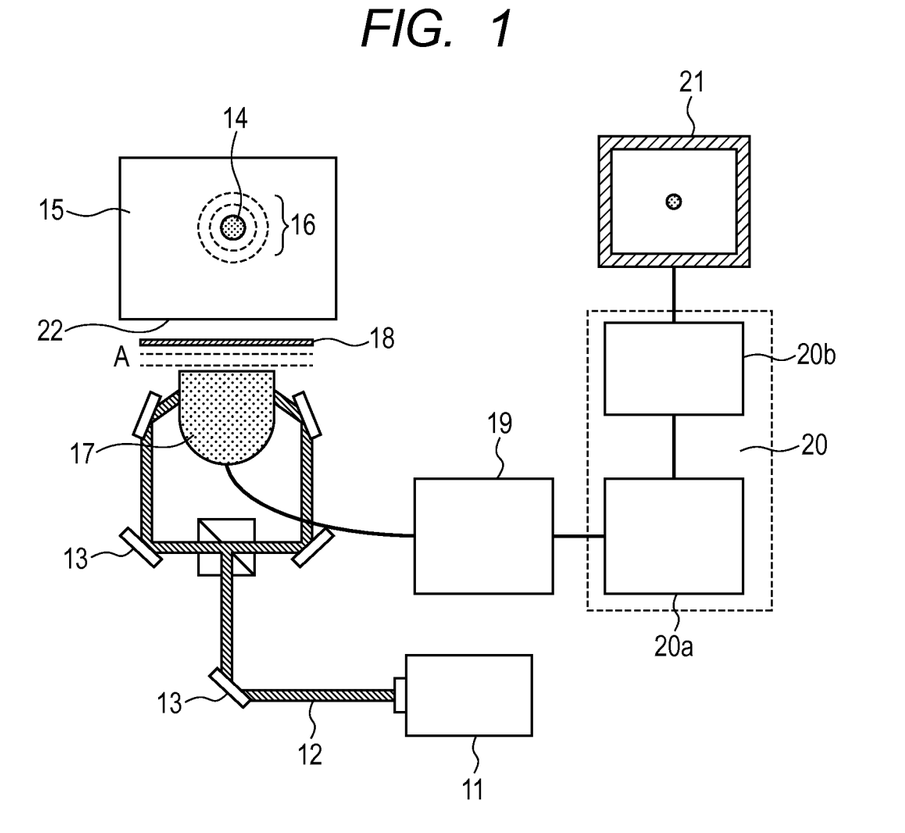
FIG. 1 is a view schematically illustrating a configuration of a subject information acquiring device according to an embodiment of the present invention.
Figure 2A:
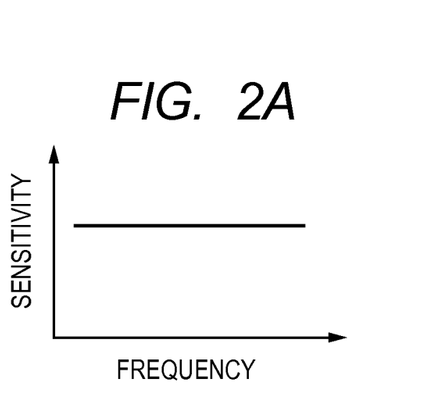
FIG. 2A is a view illustrating an example of frequency characteristics of an ideal acoustic wave probe.
Figure 2B:
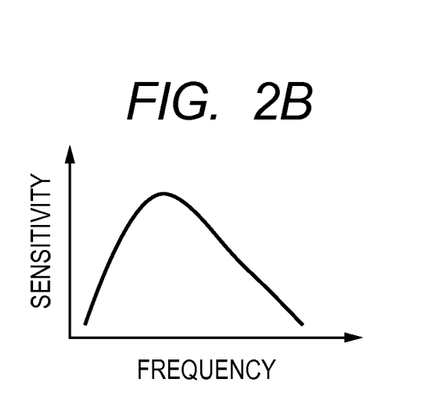
FIG. 2B is a view illustrating an example of frequency characteristics of a non-ideal acoustic wave probe.
Figure 3:
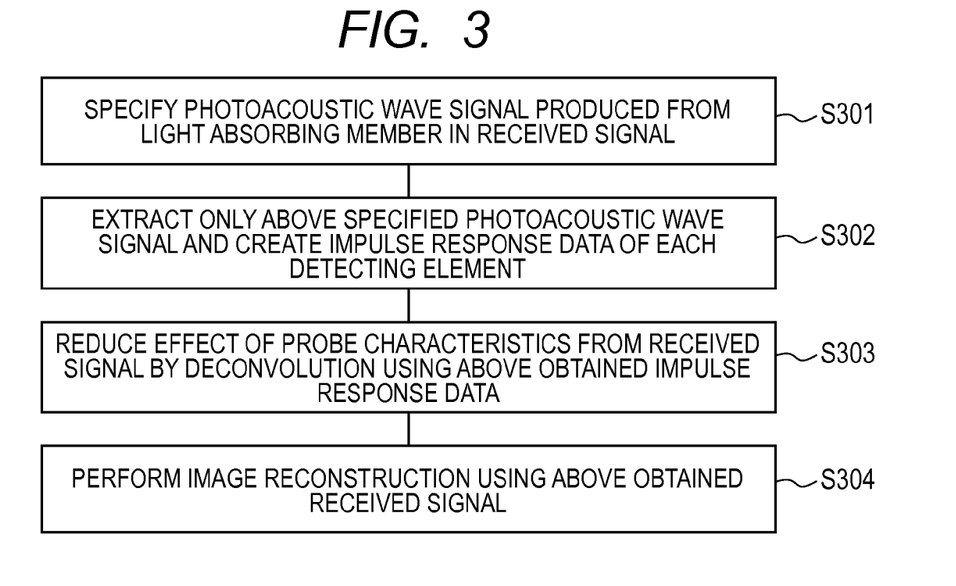
FIG. 3 is a flowchart describing an example of processing of a detection signal according to an embodiment of the present invention.

Although the acoustic wave probe preferably has the same sensitivity for acoustic waves of various frequencies as illustrated in FIG. 2A, most of commercially available acoustic wave probes have a sensitivity only for an acoustic wave of a specific frequency (also referred to as "band limitation") as illustrated in FIG. 2B. That is, the probes are not ideal. The present invention reduces image deterioration due to these characteristics of the acoustic wave probe even when a non-ideal acoustic wave probe having this band limitation is used. Further, the acoustic wave probe 17 is preferably disposed to detect acoustic waves produced from the subject 15, at various angles. For example, the acoustic wave probe is disposed such that the acoustic wave probe can move on the spherical surface 360 degrees around the subject 15. Meanwhile, when the acoustic wave probe 17 cannot be disposed to surround 360 degrees the subject 15, the acoustic wave probe may be disposed to receive acoustic waves only in a certain direction as illustrated in FIG. 1.

(Light Absorbing Member 18)

A feature of the present invention lies in providing the light absorbing member 18 outside the subject 15. The light absorbing member 18 absorbs the pulsed light 12 emitted from the light source 11, and produces a planar photoacoustic wave (for example, A in FIG. 1). Hence, the light absorbing member has a planar flat shape. Further, the light absorbing member preferably uniformly absorbs light in the plane to produce a planar wave, and also preferably it has a size larger than the detection face of the photoacoustic wave probe. The light absorbing member may directly absorb pulsed light emitted from the light source, or may absorb pulsed light reflected by a subject or pulsed light which has transmitted through the subject, depending on a mode of an arrangement of the light absorbing member in the subject information acquiring device. In the present invention, radiating pulsed light on the light absorbing member from the light source means that the light absorbing member absorbs pulsed light emitted from the light source irrespectively of the above modes. Further, the pulsed light 12 to be radiated on the light absorbing member 18 has a uniform intensity distribution, and also preferably it is radiated on an area sufficiently larger than the detection face of the acoustic wave probe 17. Further, to reduce the effect resulting from the size of the detecting element of the acoustic wave probe, the light absorbing member 18 is preferably nearly parallel to the detection face of the photoacoustic wave probe.

Any member may be used as long as the light absorbing member 18 can absorb the pulsed light 12 and an impulse and planar acoustic wave. Meanwhile, the light absorbing member preferably has a sufficiently thin optical absorption length to produce an impulse photoacoustic wave. An optical absorption thickness d of this light absorbing member is determined based on an acoustic velocity c of the optical absorber itself and a maximum detectable frequency of the acoustic wave probe 17 $f_{max}$, represented by the following equation.

$$d \leq c/(k \times f_{max})$$

Meanwhile, k refers to a proportional constant, which is typically in the range of 1 to 10. When, for example, the acoustic velocity of the optical absorber is 2500 m/sec., the maximum reception frequency of the acoustic wave probe is 5 MHz and k is 2, the absorption thickness d of the optical absorption member is 250 or less. As such, although it depends on a material, the light absorbing member has a sheet shape (flat shape). The light absorbing member 18 is preferably disposed between the acoustic wave probe 17 and subject 15 as illustrated in FIG. 1. This is because, when the photoacoustic wave produced by the light absorbing member propagates through a subject, etc. before detected, part of frequency components are absorbed by the subject, and an impulse acoustic wave is not produced. Further, the light absorbing member 18 preferably simultaneously plays a role of preventing light from being directly radiated on the acoustic wave probe 17. This is because, when light is radiated on the probe surface, a photoacoustic wave is produced from the surface of the radiated probe, thereby causing image deterioration. Hence, when the surface of the optical absorber on the subject side absorbs light, for example, when light is radiated on the subject from a subject surface direction on the opposite side of the acoustic wave probe or when light is radiated between the optical absorber and subject, light other than light to be absorbed is preferably reflected by the optical absorber in the subject direction. Hence, a metal thin film such as an aluminum foil or gold foil which has a high reflectivity of light is preferably used.

(Signal Converter 19)

The subject information acquiring device according to the present embodiment preferably has the signal converter 19 which amplifies an electrical signal obtained by the acoustic wave probe 17, and converts the electrical signal from an analog signal into a digital signal. The signal converter 19 is typically formed with, for example, an amplifier, A/D converter or Field Programmable Gate Array (FPGA) chip. When there are a plurality of detection signals obtained from the acoustic wave probe, the signal converter may preferably process multiple signals simultaneously, to thereby reduce the time to generate image data. "Detection signal" in this description is a concept which includes both of analog signals acquired from the probe 17 and digital signals obtained by AD converting the analog signals. Since the present invention targets at the photoacoustic tomography, the detection signal is "photoacoustic wave signal" of an acoustic wave produced from biological tissues which absorbed energy of radiated light. Further in the present invention, the detection signals include a first detection signal which is referred to as a "pre-deconvoluted detection signal" (described later) and a second detection signal which is referred to as a "deconvoluted detection signal."

(Signal Processing Unit 20)

The signal processing unit 20 performs processing of calculating an impulse response of each acoustic wave detecting element from the detection signal, which is characteristic processing of the present invention. The response of the acoustic wave detecting element to a planar impulse acoustic wave produced by the optical absorber is considered to be equivalent to the impulse response. In the present invention, data which the acoustic wave detecting element calculates in response to the above acoustic wave is referred to as "impulse response data". Further, the detection signal is deconvoluted utilizing the calculated impulse response data, and thereby signal deterioration due to probe characteristics is recovered. Then, image data of the interior of the subject is acquired using data obtained by restoring signal deterioration due to probe characteristics (image reconstruction). As described below, the feature of the present invention lies in that an impulse photoacoustic wave produced from the light absorbing member 18 is received by an acoustic wave probe, and the photoacoustic wave detection signal is utilized as an impulse response. In the present invention, deconvolution processing is directed to converting, by signal processing, a signal received by the acoustic wave probe having the frequency characteristics as illustrated in FIG. 2B into a signal received by the acoustic wave probe having the frequency characteristics as illustrated in FIG. 2A according.

A workstation is typically used for the signal processing unit 20, and reduction processing of a signal (photoacoustic wave signal) resulting from the photoacoustic wave and image reconstruction processing produced on the subject surface are executed by software that is in advance programmed. For example, the software used in the workstation is configured with two modules of a signal processing module 20a which performs processing of correcting deterioration of a detection signal due to probe characteristics (deconvolution in the present invention is also included in this processing) and an image reconstruction module 20b which performs image reconstruction. These modules are generally used as one program, and therefore they are usually shared. Meanwhile, noise reduction processing of a signal received at each position, which is usually performed as processing prior to image reconstruction in the photoacoustic tomography, are preferably performed by the signal processing module. To increase the efficiency of deconvolution, noise reduction processing is preferably performed before deconvolution. The image reconstruction module forms image data according to image reconstruction, and performs, for example, backprojection in a time domain or Fourier domain which are usually used in the tomography technique. When a more time can be spent for reconstruction, an image reconstruction method such as an inverse problem analyzing method by iterative processing (iterative method) can be utilized. The image reconstruction method of PAT typically includes a Fourier transform method, universal back projection method, and filtered back projection method as disclosed in NPL 1.

Depending on cases, the signal converter 19 and signal processing unit 20 may be integrated. In this case, image data of a subject can be generated by hardware processing instead of software processing which is performed by the workstation.

(Display 21)

The display 21 displays image data which is outputted from the signal processing unit 20, as an image, and, for example, a liquid crystal display is typically utilized. In addition, the display 21 may be provided separately from the subject information acquiring device according to the present invention.

(Processing of Detection Signal)

Next, processing of reducing a probe characteristic effect on a detection signal which is performed in the signal processing unit 20 and which is the feature of the present invention will be described also with reference to FIGS. 3, 4A, 4B, 4C, 5A, 5B and 5C. The following numbers match with the numbers in processing in FIG. 3.

Figure 4A:
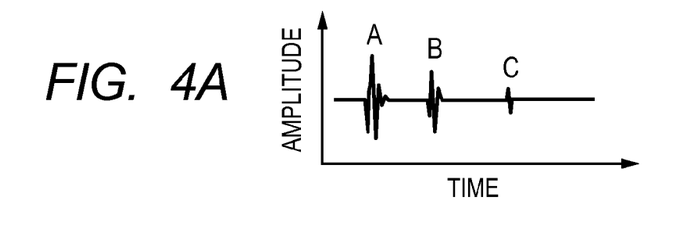
FIG. 4A is a schematic view illustrating an example of a detection signal which is a digital signal according to the present invention.

Processing I (S301): Process of Specifying a Signal (a Photoacoustic Signal Resulting from an Optical Absorber) Resulting from a Photoacoustic Wave Produced from the Light Absorbing Member 18 Among the Detection Signal Among a digital signal obtained from the signal converter 19 illustrated in FIG. 1, a photoacoustic wave signal resulting from the light absorbing member 18 is specified. FIG. 4A illustrates an example of the digital signal obtained by a given detecting element of the acoustic wave probe 17. In FIG. 4A, the horizontal axis indicates a sampling time, and the vertical axis indicates a received acoustic pressure. Generally, when pulsed light is radiated on the subject 15, a plurality of acoustic pressure signals are observed as signals as illustrated in FIG. 4A. In addition, in case of an embodiment illustrated in FIG. 1, photoacoustic waves produced from the optical absorber (such as blood in case of the biological body) inside the subject, the subject surface (such as pigments on the skin surface in case of the biological body) and light absorbing member 18 are received. In FIG. 4A, signals A, B and C indicate detection signals of photoacoustic waves produced from the light absorbing member 18, subject surface, and the optical absorbers 14 positioned interior of the subject, respectively. The point of zero of the sampling time is a pulsed light radiation time. When the ideal acoustic wave probe is used as in FIG. 2A, single N-shaped signals are theoretically assumed to be received as detections signals at A, B and C from a spherical acoustic source. Actually, while a non-ideal acoustic wave probe is used as in the present embodiment, A, B and C are not N-shaped signals and have an N-shaped like shape in which a plurality of N-shaped signals seemingly overlap, as illustrated in FIG. 4A. This is because, as described above, the probe responds only to frequency components of a specific band as illustrated in FIG. 2B. That is, an acoustic wave $p_d(t)$ detected by an actual non-ideal probe is convolution of an acoustic wave $p_{real}(t)$ detected by an ideal acoustic wave probe and an impulse response h(t) due to the probe characteristics. This can be represented as the following expression.

$$P_d(t)=P_{real}(t)*h(t)$$

Meanwhile, "*" is a symbol representing convolution. This equation indicates that a signal received by a non-ideal acoustic wave probe is distorted compared to a signal received by the ideal acoustic wave probe. Further, since signals from photoacoustic wave generation sources close to the acoustic wave detector 17 are received earlier, the sampling times of A, B and C are respectively different as illustrated in FIG. 4A. That is, the respective signals are detected at different positions in terms of time, so that it is possible to specify a detection signal of the photoacoustic wave produced from the light absorbing member 18 by utilizing this time difference. In the embodiment illustrated in FIG. 1, it is possible to easily specify based on the sampling time that the N-shaped like signal received first is a photoacoustic wave produced from the light absorbing member 18 closest to the acoustic wave detector. That is, when the distance and acoustic velocity between the light absorbing member 18 and acoustic wave detector 17 are found, a time at which the photoacoustic wave produced from the light absorbing member is observed as a signal is found out, so that it is possible to specify a signal from the light absorbing member. By performing the above processing, the photoacoustic wave signal resulting from the photoacoustic absorber member 18 is specified in the detection signal.

Figure 4B:
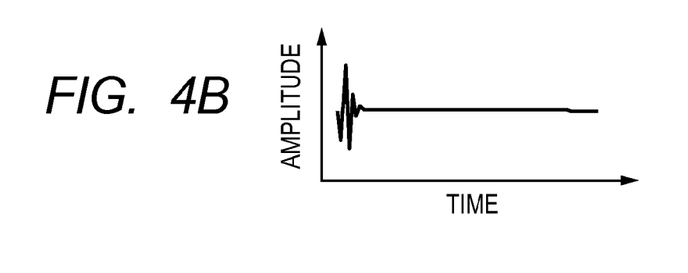
FIG. 4B is a schematic view illustrating an example of impulse response data according to the present invention.

Processing II (S302): Process of Extracting Only Data Specified in S301, and Creating Impulse Response Data of Each Detecting Element For example, data other than the signal from the light absorbing member specified in the above processing is made zero, and data (impulse response data: h(t)) in which the first reception time of the specified signal is zero is created. FIG. 4B illustrates an example of created impulse response data. As is clear from FIG. 4B, only the signal of A in FIG. 4A is clipped as data, and data values at other times are made zero. Further, a sampling start time of A is made the point of zero of the sampling time for the next signal processing. As a result, it is possible to create data as illustrated in FIG. 4B. The above data processing is performed for detection signals of all detecting elements. That is, when the number of receiving elements is one hundred, one hundred data groups as illustrated in FIG. 4B are created. It is preferable from the view point of signal processing that the number of detection signals and the number of sampling points of impulse response data are the same. By performing the above processing, it is possible to create impulse response data of each detecting element.

Processing III (S303): Process of Deconvoluting a Detection Signal Using the Above Obtained Impulse Response Data Each detection signal is corrected using impulse response data h(t) of each detecting element obtained in the processing II. This is, for example, a method of Fourier-transforming a detection signal $p_d(t)$ corresponding to the same receiving element and the impulse response data h(t) created in the processing II into frequency data $P_d(\omega)$ and $H(\omega)$, and using these items of data. In the above method, deconvolution is performed according to the following equation.

$$P_{real}(t)=\text{ifft}[P_d(\omega)/H(\omega)]$$

Meanwhile, ifft refers to inverse fast Fourier transformation, and $P_{real}(t)$ refers to a deconvoluted detection signal.

Figure 4C:
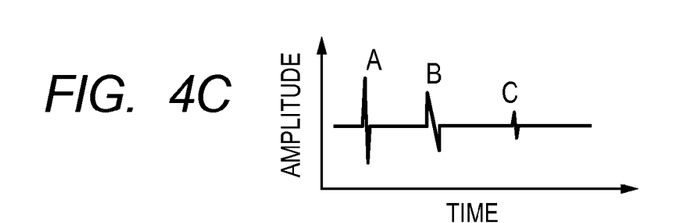
FIG. 4C is a schematic view illustrating an example of a signal obtained by deconvoluting a detection signal utilizing an impulse response acquired in the present invention.

Deconvolution is by no means limited to the above equation, and various methods such as a Wiener deconvolution method or deconvolution using iterative calculation can be utilized. FIG. 4C illustrates an example of the deconvoluted detection signal $P_{real}(t)$. Thus, by restoring a signal deteriorated due to probe characteristics by deconvolution, it is possible to convert this signal into a photoacoustic wave signal close to an N shape. In FIG. 4C, signals A, B and C indicate N-shaped detection signals of photoacoustic waves produced from the light absorbing member 18, subject surface, and the optical absorbers 14 positioned interior of the subject, respectively.

Processing IV (S304): Process of Forming Image Data Inside the Subject Using the Detection Signal Corrected in the Processing III Image reconstruction processing is performed using the deconvoluted detection signal obtained in the processing III, and image data of subject information related to an optical characteristic value distribution of the subject is formed. Since a signal for which signal deterioration due to probe characteristics is reduced as illustrated in FIG. 4C can be used, it is possible to form diagnosis image data of little image deterioration. Any image reconstruction method may be used, specifically, backprojection in a time domain or Fourier domain which is utilized in a common photoacoustic tomography can applied (see NPL 1).

When the above process is performed, even if there is no impulse response data upon measurement, it is possible to reduce an influence of probe characteristics on a detection signal by analyzing only the detection signal and convert the optical characteristic value distribution of the optical absorber inside the subject into an image without deterioration by performing image reconstruction of the detection signal from which the influence is reduced.

Example 1

Figure 5A:
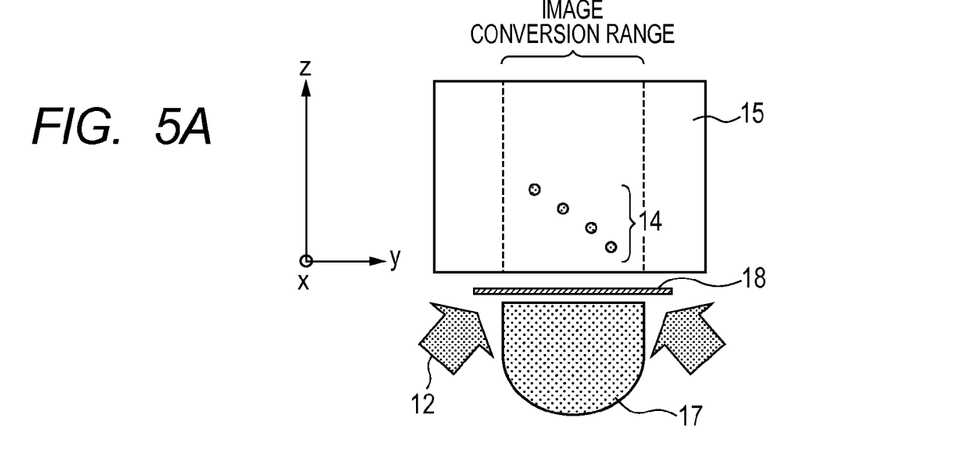
FIG. 5A is a view schematically illustrating a configuration of a subject information acquiring device according to Example 1 of the present invention.

With reference to the schematic views of the device in FIGS. 1 and 5A, an example of a subject information acquiring device using a photoacoustic tomography to which the present embodiment is applied will be described. In the present embodiment, a Q switch YAG laser which produces pulsed light of about 10 nanoseconds at the wavelength of 1064 nm was used for the light source 11. The energy of pulsed light emitted from the pulse laser light 12 was 0.6 J, and the optical system 13 was set such that this pulsed light was expanded to have the diameter of about 1 cm, using the optical system 13 such as a mirror and beam expander, and then the pulsed light was separated into two by a beam splitter to radiate on the subject directly below the probe using the mirror and prism. For the subject 15, a rectangular phantom as illustrated in FIG. 5A which simulates the biological body was used. The phantom was utilized by solidifying 1% of an intralipid by an agar. The size of the phantom was 6 cm wide, 6 cm high and 5 cm deep. In this phantom, as illustrated in FIG. 5A, four objects as the optical absorbers 14 which are solidified into columnar shapes having the diameter of 1 mm and which are colored by an ink were buried on the acoustic wave probe side. An aluminum foil was put between this phantom and probe as the light absorbing member 18. The thickness of this aluminum foil was 100 µm, having the size of 5 cm×5 cm larger than the used probe 17. This aluminum foil was disposed to reflect light in parallel to the detection face of the probe 17 as illustrated in FIGS. 1 and 5A, and such that the light reflected on the surface of the phantom was reflected again to the phantom direction, not incident on the probe 17. The phantom or acoustic wave probe was put in a water tank filled with water for acoustic matching. The pulsed light 12 was radiated on the surface of the phantom set in this way directly below the probe 17. An ultrasound transducer made of piezoelectric lead-zirconate-titanate (PZT) was used for the acoustic wave probe 17. This acoustic wave probe is a two-dimensional array type, and the number of elements is 345 (15×23) and the pitch between the elements is 2 mm. Further, the width between the elements is about 2 mm.

When the pulsed light 12 was radiated on the surface of the phantom directly below the probe 17 as illustrated in FIGS. 1 and 5A, three photoacoustic waves were produced including a photoacoustic wave produced when an aluminum foil which is the light absorbing member 18 absorbs light, a photoacoustic wave produced when the surface of the phantom on which light is radiated absorbs light, and a photoacoustic wave produced when the columnar optical absorber 14 absorbs light diffused in the phantom. The photoacoustic waves were simultaneously received by the acoustic wave probe 17 through 345 channels, and the detection signals were converted into digital data of photoacoustic wave signals through all channels using the signal converter 19 formed with an amplifier, AD converter and FPGA. To improve the S/N ratios of signals, all resulting detection signals were time-averaged by radiating laser on the signals 30 times. Then, the resulting digital data was transferred to a workstation (WS) which is the signal processing unit 20 and the data was stored in the WS.

Figure 5B:
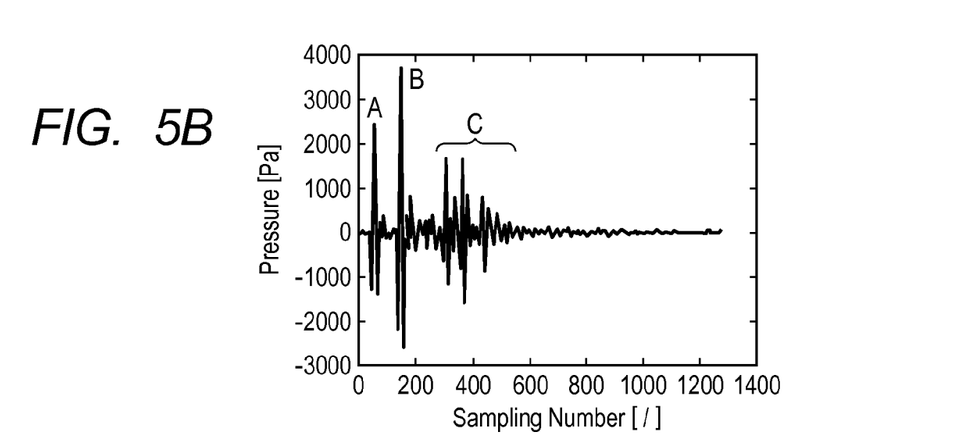
FIG. 5B illustrates an example of a detection signal according to Example 1.
Figure 5C:
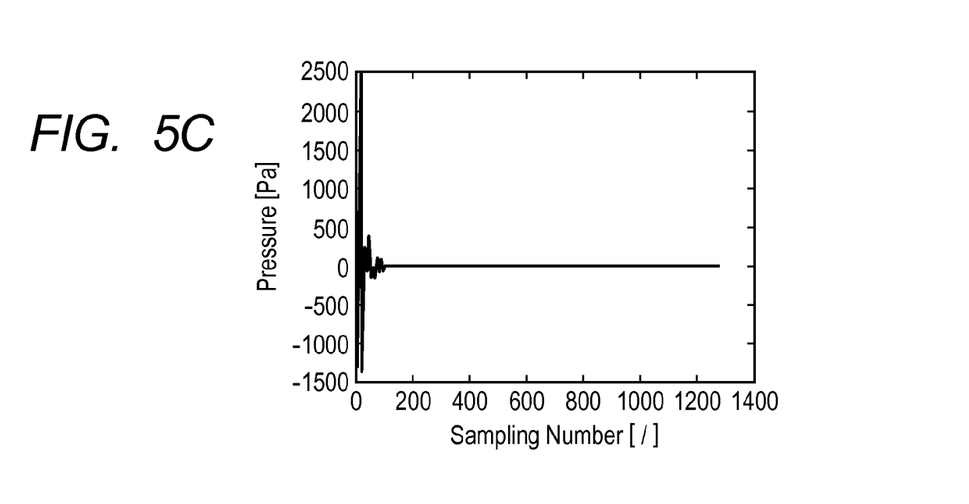
FIG. 5C illustrates impulse response data acquired in Example 1.
Figure 6A:
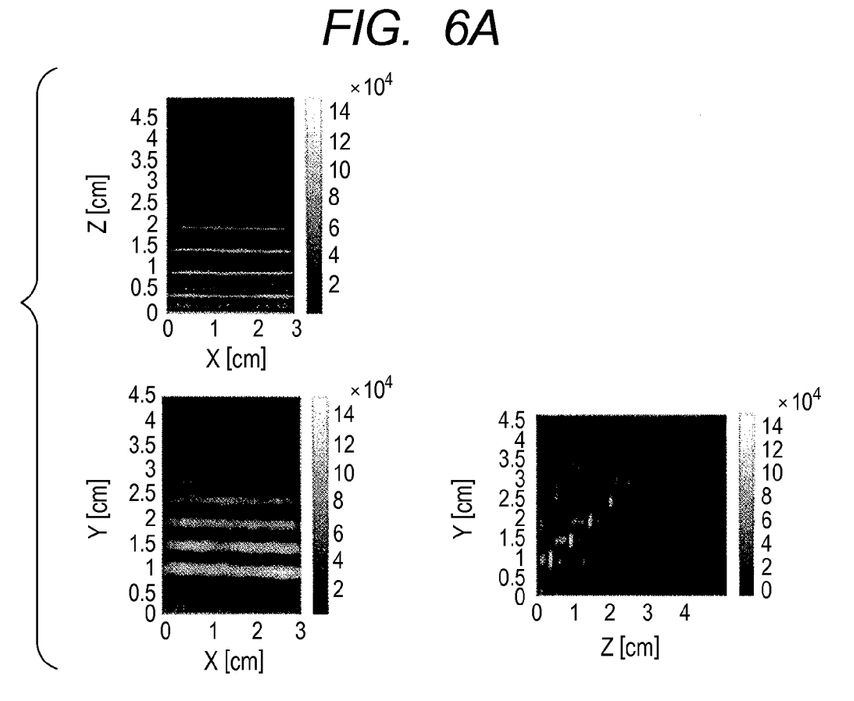
FIG. 6A illustrates an image obtained by correcting an impulse response obtained in Example 1.

FIG. 5B illustrates an example of an actually received signal. In FIG. 5B, the horizontal axis indicates the sampling time, and the vertical axis indicates the intensity of a received acoustic wave. In FIG. 5B, signal A indicates a photoacoustic signal resulting from the photoacoustic wave produced from the aluminum foil, signal B indicates a photoacoustic wave signal resulting from the photoacoustic wave produced in the surface of the phantom, and signal C indicates the photoacoustic wave signal resulting from the photoacoustic wave produced from four columnar optical absorbers disposed in the phantom. For these signals, impulse response data, in which time data other than reception time data of the A signal was made zero and the first sampling time of A was made the zero second, was created for all detection signals of 345 channels. FIG. 5C illustrates this example. Also in FIG. 5C, the horizontal axis indicate the sampling time, and the vertical axis indicates the intensity of a received acoustic wave. The impulse response data as illustrated in FIG. 5C was created per detecting element and the impulse response data were stored in a memory on the WS. Next, using each stored impulse response data, all detection signals were deconvoluted in a frequency domain, and new corrected detection data was created. Then, image reconstruction was performed using this data. Using a universal back projection method which is a time domain method, three-dimensional volume data was created. A voxel interval used in this case was 0.05 cm. The image conversion range was 3.0 cm×4.6 cm×5.0 cm. FIG. 6A illustrates an example of an image obtained at this time. FIG. 6A illustrates a Maximum Intensity Projection (MIP) image in which the three-dimensional volume data is projected in each direction and which indicates the maximum value.

Figure 6B:
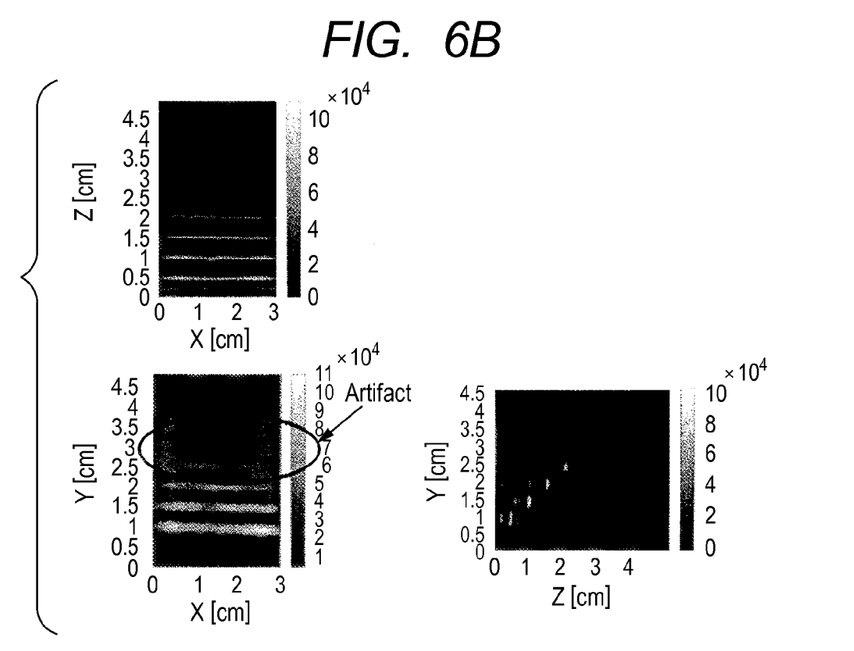
FIG. 6B illustrates an image for which an impulse response obtained in Example 1 is not corrected.

Next, image reconstruction was performed again using detection signal data stored in the WS as above, without correcting the impulse response of the detection signal. FIG. 6B illustrates an example of an image obtained at this time. Similar to FIG. 6A, FIG. 6B also illustrates a MIP image.

When FIGS. 6A and 6B are compared, in FIG. 6B, since a detection signal influenced by the probe characteristics is utilized as is, an artifact (the portion of an arrow in FIG. 6B) other than the columnar optical absorber images becomes distinct. By contrast with this, in FIG. 6A, since reduction of deterioration of a detection signal due to probe characteristics results in enabling image reconstruction using a nearly ideal photoacoustic wave signal, a distinct contrast image (artifact) other than the four columnar optical absorbers is not seen, that is, an image is substantially improved. Thus, by correcting the detection signal using the impulse response data obtained from the detection signal, it is possible to convert the optical absorber inside the subject into an image without deteriorating the image of the optical absorber.

Example 2

An example of a subject information acquiring device using a photoacoustic tomography to which the present embodiment is applied will be described. In the present embodiment, the same phantom and measuring system as in Example 1 were used. Meanwhile, to simulate a change of probe characteristics, sensitivities of amplifiers at a later stage in 80 elements corresponding to about one fourth of elements of 345 channels of the two-dimensional array detector were reduced to 50%, thereby change of sensitivity characteristics were simulated. Next, similar to Example 1, light was radiated on the phantom, and the resulting digital data was transferred to a workstation (WS) which is the signal processing unit 20 and the data was stored in the WS. Then, similar to Example 1, using the photoacoustic wave signal resulting from the optical absorber, an impulse response of each receiving element was calculated, and the detection signal was corrected using the impulse response. Further, using the corrected detection signal, image reconstruction was performed and image data was formed. As a result, the substantially same data as in FIG. 6A without deterioration can be obtained.

As described above, the present invention can reduce image deterioration due to probe characteristics even when probe characteristics change.

Example 3

An example of a subject information acquiring device using a photoacoustic tomography to which the present embodiment is applied will be described. In the present embodiment, the same phantom and measuring system as in Example 1 were used. An impulse response of a probe used in Example 1 had been measured before the probe was mounted in the measuring system, and the impulse response was stored in the WS. Next, a probe made on another day (a probe different from one used in Example 1) was mounted on the measuring system to change probe characteristics. Similar to Example 1, light was radiated on the phantom, and the resulting digital data was transferred to a workstation (WS) which is the signal processing unit 20 and the data was stored in the WS. Then, similar to Example 1, using a detection signal corrected using the photoacoustic wave signal resulting from the light absorbing member, an image was obtained. As a result, the substantially same data as in FIG. 6A without deterioration can be obtained. Next, for comparison, the detection signal was corrected using the previously measured impulse response of the probe used in Example 1, and an image was obtained using the corrected signal. When these two images were compared, the image obtained by using the detection signal corrected by the previously measured impulse response of the probe had more artifacts and a blurred image of the optical absorber compared to an image obtained by using the detection signal corrected using a photoacoustic wave signal resulting from the light absorbing member according to the present invention.

As described above, the present invention can reduce image deterioration due to probe characteristics without obtaining a new impulse response again every time a probe to be used is changed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-290254, filed Dec. 27, 2010, which is hereby incorporated by reference herein in its entirety.

REFERENCE SIGNS LIST

11 LIGHT SOURCE
17 ACOUSTIC WAVE PROBE
18 LIGHT ABSORBING MEMBER
20 SIGNAL PROCESSING UNIT

The invention claimed is:

1. A subject information acquiring device comprising:
a light absorbing member configured to be provided outside a subject;
a light source configured to irradiate the subject and said light absorbing member with pulsed light;
a detector configured to detect a subject acoustic wave produced from the subject and an absorber acoustic wave produced from said light absorbing member irradiated with the pulsed light and acquire a first detection signal based on the detected subject acoustic wave and the detected absorber acoustic wave; and
a signal processing unit configured to:
specify a signal resulting from the detected absorber acoustic wave within the first detection signal acquired by said detector;
acquire impulse response data using the specified signal;
acquire a second detection signal by de-convoluting the first detection signal using the impulse response data; and
acquire subject information using the second detection signal.

2. The subject information acquiring device according to claim 1, wherein said light absorbing member comprises at least a portion having a planar shape.

3. The subject information acquiring device according to claim 1, wherein said light absorbing member has an optical absorption thickness d that is c/fmax or less where fmax is a maximum detection frequency of said detector and c is an acoustic velocity of said light absorbing member.

4. The subject information acquiring device according to claim 1, wherein said light absorbing member is larger than at least a size of a detection face of said detector.

5. The subject information acquiring device according to claim 1, wherein said light absorbing member is parallel to a detection face of said detector.

6. The subject information acquiring device according to claim 1, wherein said light absorbing member is configured to be provided between said detector and the subject.

7. The subject information acquiring device according to claim 1, wherein said light absorbing member is configured to reflect the pulsed light toward the subject.

8. The subject information acquiring device according to claim 7, wherein said light source is configured to irradiate a back side of the subject with the pulsed light, the back side being opposite to a side of the subject facing said detector.

9. The subject information acquiring device according to claim 7, wherein said light source is configured to irradiate a space between the subject and said light absorbing member with the pulsed light.

10. The subject information acquiring device according to claim 7, wherein said light absorbing member comprises a metal.

11. The subject information acquiring device according to claim 1, wherein said light absorbing member has an optical absorption thickness d that is c/10fmax or less where fmax is a maximum detection frequency of said detector and c is an acoustic velocity of said light absorbing member.

12. The subject information acquiring device according to claim 1, wherein said signal processing unit is configured to specify the signal within the first detection signal using an acoustic velocity and a distance between said light absorbing member and said detector.

13. The subject information acquiring device according to claim 1, wherein said detector includes a plurality of transducers.

14. The subject information acquiring device according to claim 13, wherein said signal processing unit is configured to acquire the impulse response data corresponding to the plurality of transducers using the specified signal.

15. The subject information acquiring device according to claim 1, wherein said signal processing unit is configured to cause a display to display the subject information.

16. A method including processing a detection signal acquired based on a subject acoustic wave produced from a subject and an absorber acoustic wave produced from a light absorbing member provided outside the subject when the subject and light absorbing member are irradiated with pulsed light, the method comprising the steps of:
specifying a signal resulting from the detected absorber acoustic wave within the detection signal;
acquiring impulse response data using the specified signal; and
acquiring a processed detection signal by de-convoluting the detection signal using the impulse response data.

17. A non-transitory computer-readable storage medium storing a program for causing a computer to execute the method according to claim 13.

18. The method according to claim 13, further comprising the step of:
acquiring subject information using the processed detection signal.

19. The method according to claim 13, further comprising the step of:
detecting the subject acoustic wave and the absorber acoustic wave to acquire the detection signal.

* * * * *